United States Patent [19]

Bendiner

[11] Patent Number: 6,103,294
[45] Date of Patent: Aug. 15, 2000

[54] PRESERVATIVE FOR DIGESTIBLE FOOD AND BEVERAGE PRODUCTS

[75] Inventor: Bernard Bendiner, Michigan City, Ind.

[73] Assignee: Preservation Products, Inc., Michigan City, Ind.

[21] Appl. No.: 09/099,991

[22] Filed: Jun. 19, 1998

Related U.S. Application Data

[63] Continuation-in-part of application No. 08/807,426, Feb. 28, 1997, Pat. No. 5,840,249.
[51] Int. Cl.[7] ............................ H23L 1/222; A21D 13/00; A23K 1/00
[52] U.S. Cl. ............................ 426/654; 426/138; 426/615
[58] Field of Search ..................................... 426/654, 138, 426/615

[56] References Cited

U.S. PATENT DOCUMENTS

| | | | |
|---|---|---|---|
| 2,703,754 | 3/1955 | Myers | 92/1.6 |
| 3,248,277 | 4/1966 | Gärtner | 162/5 |
| 3,808,089 | 4/1974 | Von Koeppen et al. | 162/5 |
| 3,822,178 | 7/1974 | Von Koeppen et al. | 162/5 |
| 3,899,600 | 8/1975 | Sweet | 426/532 |
| 4,034,125 | 7/1977 | Ziemke et al. . | |
| 4,202,878 | 5/1980 | Ritze | 424/49 |
| 4,233,334 | 11/1980 | Owades . | |
| 4,570,573 | 2/1986 | Lohman | 119/1 |
| 4,654,207 | 3/1987 | Preston | 424/70 |
| 5,412,090 | 5/1995 | Bendiner | 536/56 |

FOREIGN PATENT DOCUMENTS

| | | |
|---|---|---|
| 131681 | 5/1946 | Australia . |
| 940250 | 10/1963 | United Kingdom . |

OTHER PUBLICATIONS

Database abstract. AN 89(09):H0142 FSTA. Journal of Food Science, 54 (3) pp. 674–678. Authors: Li et al., 1989

*Primary Examiner*—Anthony J. Weier
*Attorney, Agent, or Firm*—Brinks Hofer Gilson & Lione

[57] ABSTRACT

A process for producing cellulose pulp and a filtrate of cellulose pulp that functions as a preservative for digestible food products that are intended for human and animal consumption. In the emulsification process wax paper, water, preservative potassium sorbate and the surfactant hydroxylated lecithin are heated and blended. The cellulose pulp is filtered through a filter having openings of about 2 micrometers. The cellulose pulp acts as a preservative when used with food products such as dietary fiber, a caking agent used in the dairy industry to prevent caking and clumping of graded cheese, dry seasoning and spiced soups. The cellulose pulp can also be used to improves the flowability of products which enhances their performance in packaging. The filtrate can be used as a water base for food products and acts to preserve the food product. Also fresh fruits and vegetables can be washed with the filtrate which increases the time that they can be stored without refrigeration.

11 Claims, No Drawings

PRESERVATIVE FOR DIGESTIBLE FOOD AND BEVERAGE PRODUCTS

This application is a continuation-in-part of U.S. application Ser. No. 08/807,426, filed Feb. 28, 1997, and now U.S. Pat. No. 5,840,249, issued Nov. 24, 1998.

BACKGROUND OF THE INVENTION

This invention relates to a preservative for digestible food products that is made from substances that are currently used in food products and generally recognized as safe. The base ingredient of this preservative is cellulose which is an indigestible carbohydrate composed of carbon, hydrogen and oxygen. The chemical terminology for this natural polymer is beta-1,4-glucan. Due to the atomic arrangements at its glycosidic bonds, the bonds linking the basic units, cellulose is insoluble in water. For all practical purposes, cellulose is considered non-caloric and is considered a GRAS (generally recognized as safe) substance by the FDA. Cellulose is the principal structural component of plants and is the most abundant source of complex carbohydrates in the world. To obtain pure cellulose, this component is progressively extracted and purified from plants. During the entire extraction process, the cellulose is not dissolved. Therefore, it exists in a naturally fibrous form and exhibits characteristics common to all fibers. The length of cellulose fibers is dependent upon the extraction process, while the typical width (diameter) of cellulose fiber is approximately 15–25 microns. Powdered cellulose is currently used in the food industry as a high fiber source and/or a non-caloric bulking agent.

Most paper is made from plant fiber, most often wood, in a process that separates the cellulose from the other plant fiber material. Cellulose is the major constituent of plant fibers. Carbohydrates, including cellulose are convertible into glucose by hydrolysis, a chemical process of decomposition. Under appropriate conditions the bacteria present in the paper making process contribute to and hasten decomposition. As a result, when cellulose pulp material is maintained in a hydrous state it has a very short shelf life.

In the paper making industry biocides are added to the slurry in the pulper. A pulper is basically a vat for receiving a material that can be agitated by mechanical means and includes means for controlling the temperature. The biocides slow the deterioration of the hydrous cellulose pulp material but do not stop it. The biocides that are added to the slurry in the pulper are poisonous and thus the hydrous cellulose pulp material can not be used in many consumer products especially products intended for human consumption. Thus, not only are the biocides not effective, they are poisonous and therefore present a hazard. In the paper making process, the water is driven from the cellulose pulp and the remaining fiber is dried in a continuous operation. After the water has been removed, decomposition of the cellulose pulp ceases. However, if the process is suspended with the cellulose pulp in the hydrous state, for example over 90% water, the pulp has a very short shelf life. This short shelf life has been a major obstacle to the development of non-paper industry uses for hydrous cellulose pulp. Generally speaking, hydrous cellulose pulp is vulnerable to decomposition regardless of whether the pulp is derived from virgin vegetable constituents or from paper in a recycling operation.

Waxed paper is customarily manufactured by forming the paper sheet first then treating the sheet with an application of wax coating, either in dry or liquid form. For example, molten paraffin wax is easily applied by continuously passing a paper sheet through a molten bath of wax, removing the excess and then chilling. Such waxed papers have excellent resistance to water vapor, are free from odor, taste and toxicity and are low in cost.

At one time, waste or new waxed paper presented problems in the paper recycling industry. When waste or new wax paper was recycled waxy spots would appear on the resulting recycled paper and a wax coating would collect on the equipment thus fouling the recycling process. Consequently, the resulting recycled paper was considered inferior and it was often necessary to stop the process so that the equipment could be adequately cleaned.

This problem with recycling waste or new waxed paper was solved, however, by adding water dispersible non-ionic emulsifiers to the pulper during the repulping phase of the recycling process. The mixture containing the emulsifier is mechanically agitated at a temperature sufficiently high to melt the wax, for example from approximately 135° to 190° Fahrenheit. This process produced an emulsified wax-fiber slurry having a solids consistency of approximately 20% by weight. The hydrous cellulose pulp produced in this process for recycling waste or new waxed paper has the property of an unlimited shelf life. U.S. Pat. Nos. 3,808,089 and 3,822,178, the disclosures of which are incorporated herein by reference, fully disclose the above described process.

Various non-paper industry uses have been discovered for this hydrous cellulose pulp having an unlimited shelf life. For example, as a dispersed ingredient in toothpaste, shampoo, soap, detergent, lotions and cream products. Other non-paper industry uses that were discovered for this product were its use as artificial snow and mulch. The discovery of these non-paper industry uses of hydrous cellulose pulp having an unlimited shelf life is the subject matter of U.S. Pat. No. 5,412,090 that issued on May 2, 1995. U.S. Pat. No. 5,412,090 is hereby incorporated by reference as a part of this application. The hydrous cellulose pulp having an unlimited shelf life produced in accordance with the disclosure of U.S. Pat. No. 5,412,090 has a fiber content of about 4–6% by weight and has a fiber length of approximately 2,000 microns.

Powdered cellulose is used throughout the food industry for various functional purposes. It is the only dietary fiber used in the food industry. For example dietary fibers serve as a non caloric-bulking agent in numerous food products. Powdered cellulose is the standard caking agent used in the dairy industry to prevent caking and clumping of grated cheese, and more recently has gained popularity in dry seasoning, spiced soups and other mixtures. Powdered cellulose also improve the flowability of products, which enhances performance when packaging the product. However, as currently used in the food industry, powdered cellulose does not have a preservative attribute.

It was found that when hydrous cellulose pulp, produced in accordance with the disclosure of U.S. Pat. No. 5,412,090, is used in shampoo as a scrubbing agent, traces of fiber are left on the hair. These fibers are large enough to be visible to the consumer. This residue, although harmless, was found to be unacceptable to some consumers. It was found that if the hydrous cellulose pulp, formed in accordance with U.S. Pat. No. 5,412,090, is filtered, for example through a 2 micrometer filter, the non-toxic filtrate contains only about 0.67% hydrous cellulose pulp by weight. This hydrous cellulose is in the form of colloidal fibers and fibers that are a maximum of 10 microns in length. This filtrate retains the quality of an unlimited shelf life. However, the filtrate, like the fiber, is white in color. This was the result of some of the white wax remaining in the water phase of the filtrate. This process has been improved such that all of the wax is either on the fiber or emulsified. The colloidal fibers contained in the filtrate are transparent and thus are not, under any condition, visible to the naked eye.

Many consumer products are formed with a water base. The purest natural water includes microorganisms that will in time cause water base products to become rancid if preservatives are not added. Thus, water based consumer products commonly include a preservative. Although preservatives are chosen that most people can tolerate, some individuals are allergic to or have reactions to these preservatives. Also, the long range effect of these preservatives is often not known for certain.

A food grade preservative commonly identified as potassium sorbate and technically identified as 2,4 Hexadienoic Acid is used for example as a preservative for food products such as pickles. Potassium sorbate is commercially available in the form of a dry powder that can be placed in solution with a water based ingredient. When potassium sorbate is added to the above discussed hydrous cellulose pulp produced in accordance with the disclosure of U.S. Pat. No. 5,412,090 or its non-toxic filtrate an excellent water based preservative for consumer products is obtained. This combination of potassium sorbate and the non toxic filtrate is the subject matter of co-pending application Ser. No. 08/807, 426, filed on Feb. 28, 1997. The subject matter of co-pending applications Ser. Nos. 08/808,212 and 08/807, 426 are hereby included by reference as a part of this application.

There is a need for a powdered cellulose that acts as a preservative that can be used in the food industry.

There is also a need for a preservative that can be added to food products, intended for human consumption, that is made from natural ingredients that are safe and digestible.

Furthermore, there is a need for a water base that can be used for food products, made from natural digestible ingredients, that functions as a food preservative and is not visible to the naked eye.

Still further there is a need for a digestible food preservative that can be applied to the external surfaces of fresh fruits and vegetables that will extend the time that fresh fruits and vegetables can be stored in an un-refrigerated state.

SUMMARY OF THE INVENTION

It is an object of this invention to provide a process for producing a product and the product itself that can be used as a preservative for food intended for human as well as animal consumption.

It is also an object of this invention to provide a process for producing powdered cellulose that has a preservative attribute, and the product produced by this process, that can be used in the food industry.

It is another object of this invention to provide a process, as well as the product made by this process, that will serve as a natural ingredient preservative when applied to the outer surfaces of fresh fruits and vegetables and will not detract from the consumer's visual or taste appreciation of the fresh fruits and vegetables.

It is still another object of this invention to provide a water base for food products that will included a natural ingredient preservative and will not be visible to the human consumer.

It is another object of this invention to utilize cellulose fiber produced in a process using hydroxylated lecithin as a surfactant and potassium sorbate as a preservative as a dietary fiber, bulking agent, caking agent and to improve the flowability of products intended for human consumption.

It is another object of this invention to utilize the filtrate of hydrous cellulose pulp produced in a process using hydroxylated lecithin as a surfactant and potassium sorbate as a preservative as the water base for products intended for human consumption.

This invention consists of a process for producing a food grade preservative, that can be mixed in or applied to the surface of edible goods, that will extend the shelf life of the edible goods.

This invention further consist of a process in which the filtrate of hydrous cellulose pulp that has an unlimited shelf life is used as the water base for a liquid preservative that includes potassium sorbate and hydroxylated lecithin.

BRIEF DESCRIPTION OF THE DRAWINGS

This application does not include drawings.

DETAILED DESCRIPTION OF THE PREFERRED EMBODIMENT

During the emulsification phase of the wax paper recycling process used in practicing this invention, substantial quantities of wax are present from the waste or new waxed paper. However, this wax does not contaminate or coat the equipment even when slurries containing the emulsified product are cooled. When making waxed paper, very little wax penetrates below the surface of the un-waxed sheet of paper. However, during the emulsification phase of recycling, the paper is broken down into minute fiber filaments having irregularly shaped surfaces. Each of these minute filaments has a substantial surface area. Literally millions of fiber filaments are released from a relatively small piece of wax paper. Consequently, a piece of waxed paper having a waxed surface of 100 square inches, for example, releases fiber filaments into the emulsified slurry that have a surface area that may be as much as 1,000,000 times the original 100 square inches, or 10,000,000 square inches. The wax from the surface of the waxed paper, is melted during the emulsification phase.

Applicant's preferred embodiment is a wax paper, that is used for bakery tissue that is manufactured by Burrows Co. This wax paper utilizes sheets of paper that is thinner than that normally used and the wax is applied to the paper under pressure such that the wax impregnates the paper fiber.

During the emulsification phase of the wax paper recycling process, a surfactant must be added to the pulper. Since this product is intended for human consumption, a food grade surfactant must be used. Applicant's preferred embodiment of food grade surfactant is a hydroxylated soybean lecithin that has high emulsifying and dispersing properties in aqueous systems.

Such an emulsifier is produced and sold by Lucas Meyer Inc. of Decatur, Ill. 62524 under their trademark "EMULFLUID HL 66". EMULFLUID HL 66 is a hydroxylated soybean lecithin with high emulsifying and dispersing properties in aqueous systems. EMULFLUID HL 66 is generally recognized as safe (GRAS) as a multi-purpose food additive under Title 21 CFR 172.814.

In the emulsification phase of the process there is a bonding of the water, wax, cellulose fiber, sorbate and the hydroxylated soybean lecithin into a mechanism that eliminates oxygen from being dissolved in the ingredient in both the fiber state and the filtrate state. Since no oxygen can be dissolved in the ingredient, microorganisms cannot live in this ingredient. The ingredient is not toxic and thus does not kill microorganisms, rather it inhibits their continued existence as a result of the lack of oxygen. As a result of this lack of oxygen the ingredient functions as an anti-microbial preventive and as an anti-oxidation compound. The anti-oxidation aspect of this ingredient can best be illustrated by placing a non-galvanized nail in the filtrate. The non-galvanized nail will not rust whereas if a non-galvanized nail is placed in any tap water, it will rust.

This hydrous cellulose pulp is 95% water, 4.67% fiber and 0.32% wax. The hydrous cellulose pulp can be filtered through a 2 micrometer (0.000002 meters) filter and the resulting filtrate is then used as the water base for the preservative for digestible food products. This filtrate is approximately 99% water, 0.68% fiber and 0.32% wax.

The filtrate is free of microorganisms such as bacteria and fungi, possesses an unlimited shelf life, and may be produced either by recycling waste or new waxed paper or by processing virgin vegetable constituents in the presence of wax during the emulsification phase of the defibering process.

It appears that an electric kinetic suspension has been created that has a barrier bonding mechanism that prevents oxygen from the air from dissolving in the water and the oxygen in the water from freeing itself. The filtrate is, as a result of this electric kinetic suspension, impervious to microbiological and corrosive attacks. The filtrate, which is 99% water, and contains minute portions of fiber coated with a thin micro-molecular layer of wax derived from this process, is non toxic and has an unlimited shelf life and thus can be utilized as the water base for products and provide the product with an unlimited shelf life.

In accordance with this invention, the starting waxed paper that can be used is the waxed tissue paper used in bakeries and delicatessens to wrap food products is preferred. However, any waxed paper that has been coated with a food grade paraffin wax, designated as a dry wax, can be used. Waste or new waxed paper can be used in the preferred embodiment and is obtained directly from the paper producing facilities. For example, trimmings from a trimming machine or wax paper that did not meet required test standards may be used. Such waxed paper is free of printing and thus is clean. The waxed paper is added to a pulper. A pulper is basically a vat for receiving a material that can be agitated by mechanical means and includes means to control the temperature. The process of pulping is essentially one of separating cells from intercellular material. It should be understood that any equipment such as a conventional high speed pulper may be used. The temperature of the wax-containing fiber slurry is raised to a temperature above the melting point of the wax and beating is continued until the wax and fiber are released into the aqueous solution. The resulting water-fiber slurry can then be subjected to a washing process to remove any impurities. Newly manufactured wax paper does not need this washing process.

The process of the present invention encompasses the use of 100% waxed paper stock having a wax content of up to 30% by weight. However, non-waxed waste paper, in modest proportions can be used without affecting the outcome. Non waxed fiber products can be used as a starting product and a paraffin wax in the correct ratio to fiber can be added. The use of waxed paper as a starting point has the advantage that it contains the proper ratio of fiber to wax and it is available at economical rates.

Cellulose fibers is white in color. The water phase of the filtrate includes emulsified wax which is transparent. Thus, the filtrate can be used as a water based food preservative, intended for human consumption, or to be applied to the external surfaces of fresh fruits and vegetables and appear as a clear liquid. It has been found that for food products intended for human consumption a water base that does not appear to be crystal clear is objectionable. Since this product is intended for human consumption, solving this problem is rendered difficult since only food grade ingredients can be utilized and even some food grade ingredients will introduce objectionable attributes into the product such as an unacceptable taste or medical side effects. Furthermore, any ingredient that is added to the product must be digestible.

After the process for producing the hydrous cellulose pulp has been completed, it is filtered through a very fine filter, for example a 2 micrometer (0.000002 meters) filter to remove the larger portions of hydrous cellulose pulp, leaving a filtrate that is free of microorganisms and includes only minute fiber portions. Although a 2 micrometer filter is used in the preferred embodiment it should be understood that a very fine filter is required but it need not be precisely 2 micrometers. The filtrate has a very low viscosity and can be readily sprayed through conventional nozzles.

While the invention has heretofore been described in detail with particular reference to specific products, it is to be understood that variations, modifications and the use of equivalents can be effected without departing from the scope of this invention. It is, therefore, intended that such changes and modifications be covered by the following claims.

I claim:

1. A cellulose pulp that acts as a preservative for digestible food products comprising:
   cellulose pulp material that was produced in an emulsification process from a mixture of wax paper, water, potassium sorbate, and a food grade surfactant hydroxylated soybean lecithin;
   the emulsification process having functioned to bond the water, wax, cellulose fiber and the hydroxylated soybean lecithin into a mechanism that eliminates oxygen, thus resulting in a cellulose pulp that is free of oxygen.

2. A cellulose pulp that acts as a preservative for digestible food products as set forth in claim 1, wherein:
   the amount of potassium sorbate is in the range of 0.1%–5% by weight of the cellulose pulp material.

3. A cellulose pulp that acts as a preservative for digestible food products as set forth in claim 1, wherein:
   the amount of hydroxylated soybean lecithin is in the range of 0.01% to 0.10% by weight of the cellulose pulp material.

4. A cellulose pulp that acts as a preservative for digestible food products as set forth in claim 2 wherein the amount of hydroxylated soybean lecithin is in the range of 0.01% to 0.10% by weight of the cellulose pulp material.

5. A preservative for digestible food products comprising:
   a filtrate of a decomposition resistant hydrous cellulose pulp material that was produced in an emulsification process from a mixture of wax paper, water, potassium sorbate, and hydroxylated soybean lecithin;
   the emulsification process having functioned to bond the water, wax, cellulose fiber and the hydroxylated soybean lecithin into a mechanism that eliminates oxygen, thus resulting in a cellulose pulp that is free of oxygen.

6. A preservative for digestible food products as set forth in claim 5 wherein the amount of potassium sorbate is in the range of 0.1%–5% by weight of the filtrate.

7. A preservative for digestible food products as set forth in claim 5 wherein the amount of hydroxylated soybean lecithin is in the range of 0.01% to 0.10% by weight of the filtrate.

8. A preservative for digestible food products as set forth in claim 6 wherein the amount of hydroxylated soybean lecithin is in the range of 0.01% to 0.10% by weight of the filtrate.

9. The preservative for digestible food products as set forth in claim 5 wherein:
the filtrate of a decomposition resistant hydrous cellulose pulp material has passed through a filter that has opening of about 2 micrometers.

10. The preservative for digestible food products as set forth in claim 5 wherein:
said filtrate of a decomposition resistant hydrous cellulose pulp material is filtered from a decomposition resistant hydrous cellulose pulp material that was produced in a process that used a water soluble non-ionic emulsifier.

11. The preservative for digestible food products as set forth in claim 6 wherein:
said filtrate of a decomposition resistant hydrous cellulose pulp material is filtered from a decomposition resistant hydrous cellulose pulp material that was produced in a process that used a water soluble non-ionic emulsifier.

* * * * *